(12) United States Patent
Giardina et al.

(10) Patent No.: US 6,432,977 B1
(45) Date of Patent: Aug. 13, 2002

(54) SALTS OF QUINOLINE DERIVATIVES AS NK3 ANTAGONISTS

(75) Inventors: Giuseppe Arnaldo Maria Giardina; Carlo Farina, both of Milan; M. Grugni, Verbania; Luca Francesco Raveglia, Milan, all of (IT)

(73) Assignee: SmithKline Beecham S.p.A., Baranzate di Bollate (IT)

( * ) Notice: Subject to any disclaimer, the term of this patent is extended or adjusted under 35 U.S.C. 154(b) by 0 days.

(21) Appl. No.: 09/994,076

(22) Filed: Nov. 6, 2001

Related U.S. Application Data

(63) Continuation of application No. 09/077,152, filed as application No. PCT/EP96/05210 on Nov. 22, 1996.

(30) Foreign Application Priority Data

Nov. 24, 1995 (GB) ................................. 9524137

(51) Int. Cl.[7] ........................ A61K 31/47; A61K 31/445

(52) U.S. Cl. ........................................ 514/311; 514/312

(58) Field of Search .................................. 514/311, 312

(56) References Cited

FOREIGN PATENT DOCUMENTS

| WO | 95/32948 | * | 12/1995 |
| WO | WO 95 32948 | | 12/1995 |
| WO | 96/02509 | * | 2/1996 |

OTHER PUBLICATIONS

U.S. application No. 08/737,658, Giardina et al., filed May 23, 1995.
U.S. application No. 08/450,438, Giardina et al., filed May 25, 1995.
U.S. application No. 08/450,937, Giardina et al., filed May 25, 1995.
U.S. applicaton No. 08/451,938, Giardina et al., filed May 25, 1995.
U.S. application No. 08/988,551, Giardina et al., filed Dec. 10, 1997.

* cited by examiner

*Primary Examiner*—D. Margaret Seaman
(74) *Attorney, Agent, or Firm*—Nora Stein-Fernandez; Stephen A. Venetianer; Charles M. Kinzig

(57) ABSTRACT

A compound of formula (I) or a solvate thereof, characterized in that salt comprises a compound of formula (I) in anionic form and a salting cation; a process from preparing such a compound, a pharmaceutical composition containing such a compound and the use of such a compound in medicine.

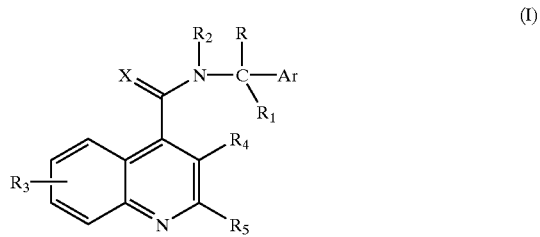

(I)

3 Claims, No Drawings

SALTS OF QUINOLINE DERIVATIVES AS NK3 ANTAGONISTS

This application is a continuation of Ser. No. 09/077,152 filed May 21, 1998 which is a national stage of PCT/EP96/05210 filed Nov. 22, 1996.

The present invention relates to novel compounds, in particular to salts of quinoline derivatives, to a process for the preparation of such compounds, to pharmaceutical compositions containing such compounds and to the use of such compounds and compositions in medicine.

The mammalian peptide Neurokinin B (NKB) belongs to the Tachykinin (TK) peptide family which also include Substance P (SP) and Neurokinin A (NKA). Pharmacological and molecular biological evidence has shown the existence of three subtypes of TK receptor ($NK_1$, $NK_2$ and $NK_3$) and NKB binds preferentially to the $NK_3$ receptor although it also recognises the other two receptors with lower affinity (Maggi et al, 1993, *J. Auton. Pharmacol.*, 13, 23–93).

Selective peptidic $NK_3$ receptor antagonists are known (Drapeau, 1990 *Regul. Pept.*, 31, 125–135), and findings with peptidic $NK_3$ receptor agonists suggest that NKB, by activating the $NK_3$ receptor, has a key role in the modulation of neural input in airways. skin, spinal cord and nigrostriatal pathways (Myers and Undem, 1993, *J.Phisiol.*, 470, 665–679; Counture et al., 1993, *Regul. Peptides*, 46, 426–429; Mccarson and Krause, 1994, *J. Neurosci.*, 14 (2), 712–720; Arenas et al. 1991, *J.Neurosci.*, 11, 2332–8).

However, the peptide-like nature of the known antagonists makes them likely to be too labile from a metabolic point of view to serve as practical therapeutic agents.

International Patent Application Number PCT/EP95/02000 describes certain quinoline derivatives and describes inter alia the preparation of the quinolines and their use in medicine. The disclosures of PCT/EP95/02000 are relevant to the present application only by virtue of Article 54(3) of the European Patent Convention.

We have now discovered certain novel salts of the quinoline derivatives of the compounds of PCT/EP95/02000. The new salts are selective, non-peptide $NK_3$ antagonists which are far more stable from a metabolic point of view than the known peptidic $NK_3$ receptor antagonists and are of potential therapeutic utility in treating pulmonary disorders (asthma, chronic obstructive pulmonary diseases -COPD-, airway hyperreactivity, cough), skin disorders and itch (for example, atopic dermatitis and cutaneous wheal and flare), neurogenic inflammation and CNS disorders (Parkinson's disease, movement disorders, anxiety, psychosis). These disorders are referred to hereinafter as the Primary Disorders.

The novel $NK_3$ antagonists of the present invention are also of potential therapeutic utility in treating convulsive disorders (for example epilepsy), renal disorders, urinary incontinence, ocular inflammation, inflammatory pain, eating disorders (food intake inhibition), allergic rhinitis, neurodegenerative disorders (for example Alzheimer's disease), psoriasis, Huntington's disease, and depression (hereinafter referred to as the Secondary Disorders).

The compounds of the present invention are also useful in the prevention and treatment of disorders of the central nervous system, such as schizophrenia; neurodegenerative disorders, such as AIDS related dementia, senile dementia of the Alzheimer type and Down's syndrome; demyelinating diseases such as multiple sclerosis and other neuropathological disorders such as diabetic or peripheral neuropathy, AIDS related neuropathy, chemotherapy-induced neuropathy and neuralgia; respiratory diseases such as, bronchopneumonia and bronchospasm; inflammatory diseases such as inflammatory bowel disease, fibrositis, osteoarthritis, rheumatoid arthritis; allergies such as eczema and rhinitis; hypersensivity disorders such as poison ivy; ophthalmic diseases such as conjunctivitis, vernal conjuctivitis and the like; cutaneous diseases such as contact dermatitis, urticaria and other eczematoid dermatitis; addiction disorders such as alcoholism; stress related somatic disorders; reflex sympathetic dystrophy such as shoulder/hand syndrome; dysthymic disorders; adverse immunological reactions such as rejection of transplanted tissues and disorders related to immune enhancment or suppression such as systhemic lupus erythematosis; gastrointestinal (GI) disorders and diseases of the GI tract such as disorders associated with the neuronal control of viscera such as ulcerative colitis, Crohn's disease; disorders of the bladder function; fibrosing and collagen diseases such as scleroderma and eosinophilic fascioliasis; disorders of the blood flow caused by vasodilation and vasospastic diseases such as angina, migraine and Reynaud's disease; pain or nociception, for example, that is attributable to or associated with any of the foregoing conditions especially the transmission of pain in mioraine (hereinafter referred to as the 'Further Disorders').

According to the present invention there is provided a salted form of a compound of formula (I) (hereinafter also referred to as 'a Salt of the invention'):

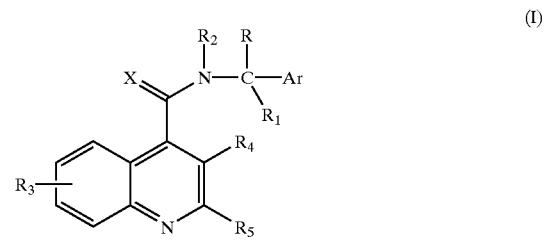

(I)

or a solvate thereof, wherein Ar is an optionally substituted phenyl, naphthyl or $C_{5-7}$ cycloalkdienyl group, or an optionally substituted single or fused ring heterocyclic group, having aromatic character, containing from 5 to 12 ring atoms and comprising up to four heteroatoms in the or each ring selected from S, O, N;

R is linear or branched $C_{1-8}$ alkyl, $C_{3-7}$ cycloalkyl, $C_{4-7}$ cycloalkylalkyl, optionally substituted phenyl or phenyl $C_{1-6}$ alkyl, an optionally substituted five-membered heteroaromatic ring comprising up to four heteroatom selected from O and N, hydroxy $C_{1-6}$ alkyl, amino $C_{1-6}$ alkyl, $C_{1-6}$ alkylaminoalkyl, di $C_{1-6}$ alkylaminoalkyl, $C_{1-6}$ acylaminoalkyl, $C_{1-6}$ alkoxyalkyl, $C_{1-6}$ alkylcarbonyl, carboxy, $C_{1-6}$ alkoxyxcarbonyl, $C_{1-6}$ alkoxycarbonyl $C_{1-6}$ alkyl, aminocarbonyl, $C_{1-6}$ alkylaminocarbonyl, di $C_{1-6}$ alkylaminocarbonyl, halogeno $C_{1-6}$ alkyl; or is a group —$(CH_2)_p$— when cyclized onto Ar, where p is 2 or 3;

$R_1$ and $R_2$, which may be the same or different, are independently hydrogen or $C_{1-6}$ linear or branched alkyl, or together form a —$(CH2)_n$— group in which n represents 3, 4, or 5; or $R_1$ together with R forms a group —$(CH_2)_q$—, in which q is 2, 3, 4 or 5.

$R_3$ and $R_4$, which may be the same or different, are independently hydrogen, $C_{1-6}$ linear or branched alkyl, $C_{1-6}$ alkenyl, aryl, $C_{1-6}$ alkoxy, hydroxy, halogen, nitro, cyano, carboxy, carboxamido, sulphonamido, $C_{1-6}$ alkoxycarbonyl, trifluoromethyl, acyloxy, phthalimido, amino, mono- and di-$C_{1-6}$ alkylamino, —$O(CH_2)_r$—

$NT_2$, in which r is 2, 3, or 4 and T is hydrogen or $C_{1-6}$ alkyl or it forms with the adjacent nitrogen a group

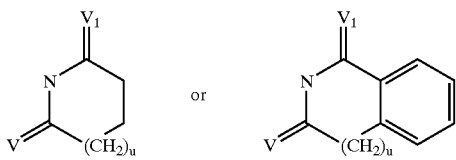

in which V and $V_1$ are independently hydrogen or oxygen and u is 0,1 or 2; —$O(CH_2)_s$—OW in which s is 2, 3, or 4 and W is hydrogen or $C_{1-6}$ alkyl; hydroxyalkyl, aminoalkyl, mono-or di-alkylaminoalkyl, acylamino, alkylsulphonylamino, aminoacylamino, mono- or di-alkylaminoacylamino; with up to four $R_3$ substituents being present in the quinoline nucleus; or $R_4$ is a group —$(CH_2)_t$— when cyclized onto $R_5$ as aryl, in which t is 1, 2, or 3;

$R_5$ is branched or linear $C_{1-6}$ alkyl, $C_{3-7}$ cycloalkyl, $C_{4-7}$ cycloalkylalkyl, optionally substituted aryl, or an optionally substituted single or fused ring heterocyclic group, having aromatic character, containing from 5 to 12 ring atoms and comprising up to four hetero-atoms in the or each ring selected from S, O, N;

X is O, S, or N—C≡N; characterised in that the salt comprises a compound of formula (I) in anionic form and a salting cation.

Suitably, the salt is a compound of formula (A):

$$S^{t-} M^{t+} \qquad (A)$$

or a solvate thereof, wherein;

t is an integer 1, 2 or 3;

$M^{t+}$ is a salting cation; and $S^{t-}$ is an anion provided by an appropriate compound of the above defined formula (I).

Suitable salting cations $M^{t+}$ include metal ions and organic cations, in particular pharmaceutically acceptable metal ions and organic cations.

Suitable pharmaceutically acceptable metal ions include those ions provided by aluminium, alkali metals such as lithium, sodium or potassium, alkaline earth metals such as calcium or magnesium.

Suitable pharmaceutically acceptable organic cations include ammonium or substituted ammonium ions, for example those from lower alkylamines such as triethylamine, hydroxy alkylamines such as 2-hydroxyethylamine, bis-(2-hydroxyethyl)-amine or tri-(2-hydroxyethyl)-amine, cycloalkylamines such as bicyclohexylamine, or with procaine, dibenzylpiperidine, N-benzyl-β-phenethylamine, dehydroabietylamine, N,N'-bisdehydroabietylamine, glucamine, N-methylglucamine or bases of the pyridine type such as pyridine, collidine, quinine or quinoline.

A particular salting cation $M^{t+}$ is an alkali metal ion, for example a sodium ion.

An appropriate compound of formula (A) is a compound which is capable of forming an anion $S^{t-}$ and favourably includes compounds of formula (A) which comprise acidic moieties, for example those which comprise a carboxy group and/or a phenolic hydroxy group.

Suitably, t is 1 or 2, for example 1.

Particular values for the variables of formula (I) are set out below. It sill be appreciated that any appropriate compound of formula (I) comprising these variables will be characterised in that it is capable of forming a anion $S^{t-}$. Thus:

Examples of Ar are phenyl, optionally substituted by hydroxy, halogen, $C_{1-6}$ alkoxy or $C_{1-6}$ alkyl. Examples of halogen are chlorine and fluorine, an example of $C_{1-6}$ alkoxy is methoxy and an example of $C_{1-6}$ alkyl is methyl.

Examples of Ar as a heterocyclic group are thienyl and pyridyl.

Examples of Ar as a $C_{5-7}$ cycloalkdienyl group is cyclohexadienyl.

Examples of R are as follows:

$C_{1-8}$ alkyl: methyl, ethyl, n-propyl, iso-propyl, n-butyl, heptyl;

phenyl $C_{1-6}$ alkyl: benzyl;

hydroxy $C_{1-6}$ alkyl: $CH_2OH$, —$CH_2CH_2OH$, CH(Me)OH;

amino $C_{1-6}$ alkyl: —$CH_2NH_2$;

di $C_{1-6}$ alkylaminoalkyl: —$CH_2NMe_2$;

$C_{1-6}$ alkoxylalkyl: $CH_2OMe$;

$C_{1-6}$ alkylcarbonyl: COMe;

$C_{1-6}$ alkoxycarbonyl: COOMe;

$C_{1-6}$ alkoxycarbonyl $C_{1-6}$ alkyl: $CH_2COOMe$;

$C_{1-6}$ alkylaminocarbonyl: CONHMe;

di $C_{1-6}$ alkylaminocarbonyl: $CONMe_2$, CO(1-pyrrolidinyl);

halogen $C_{1-6}$ alkyl: trifluoromethyl;

—$(CH_2)_p$— when cyclized onto Ar:

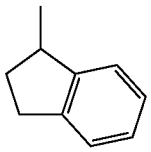

Example of $R_1$ and $R_2$ as $C_{1-6}$ alkyl is methyl; example of $R_1$ together with R forming a group—$(CH_2)_q$— is spirocyclopentane.

Examples of $R_3$ and $R_4$ are methyl, ethyl, n-propyl, n-butyl, methoxy, hydroxy, amino, chlorine, fluorine, bromine, acetyloxy, 2-(dimethylamino)ethoxy, 2-(phthalimido)ethoxy, aminoethoxy, 2-(1-pyrrolidinyl)ethoxy, phthalimido, dimethylaminopropoxy, dimethylaminoacetylamino, acetylamino, dimethylaminomethyl and phenyl.

Examples of $R_5$ are cyclohexyl, phenyl optionally substituted as defined for Ar above; examples of $R_5$ as a heterocyclic group are furyl, thienyl, pyrryl, thiazolyl, benzofuryl and pyridyl.

A preferred group compounds of formula (I) are those in which:

Ar is phenyl, optionally substituted by $C_{1-6}$ alkyl or halogen; thienyl or a $C_{5-7}$ cycloalkdienyl group;

R is $C_{1-6}$ alkyl, $C_{1-6}$ alkoxycarbonyl, $C_{1-6}$ alkylcarbonyl, hydroxy $C_{1-6}$ alkyl;

$R_1$ and $R_2$ are each hydrogen or $C_{1-6}$ alkyl;

$R_3$ is hydrogen, hydroxy, halogen, $C_{1-6}$ alkoxy, $C_{1-6}$ alkyl;

$R_4$ is hydrogen, $C_{1-6}$ alkyl, $C_{1-6}$ alkoxy, hydroxy, amino, halogen, aminoalkoxy, mono- or di-alkylaminoalkoxy, mono- or di-alkylaminoalkyl, phthalimidoalkoxy, mono- or di-alkylaminoacylamino and acylamino;

$R_5$ is phenyl, thienyl, furyl, pyrryl and thiazolyl.

A further preferred group of compounds of formula (I) are those in which:

Ar is phenyl, 2-chlorophenyl, 2-thienyl or cyclohexadienyl;

R is methyl, ethyl, n-propyl, —COOMe, —COMe;

$R_1$ and $R_2$ are each hydrogen or methyl;

$R_3$ is hydrogen, methoxy, or hydroxy;

$R_4$ is hydrogen, methyl, ethyl, methoxy, hydroxy, amino, chlorine, bromine, dimethylaminoethoxy, 2-(phthalimido)ethoxy, aminoethoxy, 2-(1-pyrrolidinyl)ethoxy, dimethylaminopropoxy, dimethylaminoacetylamino, acetylamino, and dimethylaminomethyl.

$R_5$ is phenyl, 2-thienyl, 2-furyl, 2-pyrryl, 2-thiazolyl and 3-thienyl; and X is oxygen.

A preferred sub-group of compounds within the scope of formula (I) above is of formula (Ia):

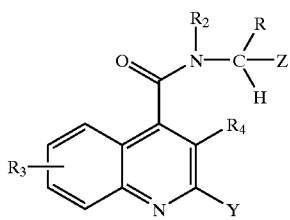

(Ia)

in which:

R, $R_2$, $R_3$ and $R_4$ are as defined in formula (I), and Y and Z, which may be the same or different, are each Ar as defined in formula (I).

A particularly preferred group of compounds of formula (Ia) are those of formula (Ib) in which the group R is oriented downward and H upward.

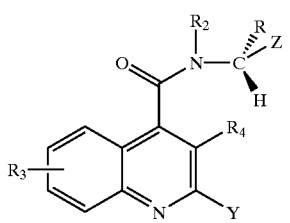

(Ib)

The compounds of formula (I) or their solvates are preferably in pharmaceutically acceptable or substantially pure form. By pharmaceutically acceptable form is meant, inter alia, of a pharmaceutically acceptable level of purity excluding normal pharmaceutical additives such as diluents and carriers, and including no material considered toxic at normal dosage levels.

One particular compound is (S)-(−)-N-(α-ethylbenzyl)-3-hydroxy-2-phenyl-4-quinoline carboxamide.

A substantially pure form will generally contain at least 50% (excluding normal pharmaceutical additives), preferably 75%, more preferably 90% and still more preferably 95% of the Salt of the invention or a solvate thereof.

One preferred pharmaceutically aceptable form is the crystalline form, including such form in pharmaceutical composition. In the case of salts and solvates the additional ionic and solvent moieties must also be non-toxic.

Suitable solvates are pharmaceutically acceptable solvates.

Examples of pharmaceutically acceptable solvates of a Salt of the invention include hydrates, such as sesquihydrates.

The compounds of formula (I) may have at least one asymmetric centre and therefore may exist in more than one stereoisomeric form. The compounds of formula (A) include all such forms and mixtures thereof, including racemates.

The invention also provides a process for the preparation of a Salt of the invention, or a solvate thereof, which process comprises admixing a source of $S^{t-}$ anions and a source of salting cations $M^{t+}$; and thereafter, as required, preparing a solvate of the Salt of the invention so formed.

Suitable conditions for preparing the salt of formula (A) include conventional salification methods, the particular conditions used being dependent upon the particular nature of the salting ions chosen, in particular the source of $S^{t-}$ Generally, the source of $S^{t-}$ ions and source of salting cation $M^{t+}$ are admixed in an alkanol, suitably an alkanol containing water, at any temperature providing a suitable rate of formation of the required product, usually at ambient temperature or a slightly elevated temperature, such as a temperature in the range of from 25 to 50° C., for example 40° C.

When the salting cation $M^{t+}$ is a metal ion, a suitable source of $M^{t+}$ is a metal hydroxide, for example sodium hydroxide for compounds where $M^{t+}$ is sodium.

Suitable alkanols are $C_{1-3}$ alkanols, for example methanol.

When the solvent is an alkanol it may contain up to 25% by volume, more usually up to 10% by volume, of water.

Conveniently, a solution of the source of salting cation $M^{t+}$ ions in water is admixed with a solution of the appropriate compound of formula (I) in an alkanol.

The resulting product may be obtained by conventional crystallisation/recrystallisation methods.

Conveniently, the product is crystallised from the reaction solvent. Recrystallisation is conveniently effected using an alternative solvent such as toluene or isopropanol or mixtures thereof.

A suitable source of $S^{t-}$ ions is a compound of formula (I) which comprises a carboxy group and/or a phenolic hydroxy group.

A compound of formula (I) may be prepared by reacting a compound of formula (III):

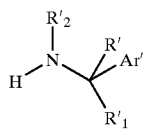

(III)

in which R', $R'_1$, $R'_2$ and Ar' are R, $R_1$, $R_2$ and Ar as defined for formula (I) or a group or atom convertible to R, $R_1$, $R_2$ and Ar, with a compound of formula (II)

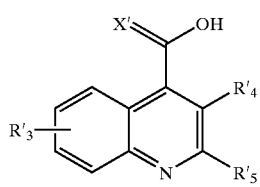

(II)

or an active derivative thereof, in which $R'_3$, $R'_4$, $R'_5$ and X' are $R_3$, $R_4$, $R_5$ and X as defined for formula (I) or a group convertible to $R_3$, $R_4$, $R_5$ and X, to form a compound of formula (Ic)

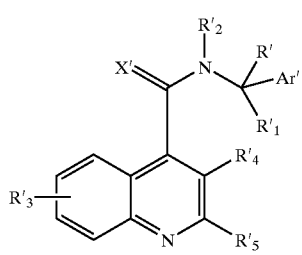

(Ic)

and optionally thereafter performing one or more of the following steps:

(a) where R', R'$_1$ to R'$_5$, Ar' and X' are other than R, R$_1$ to R$_5$, Ar and X, converting any one of R', R'$_1$ to R'$_5$, Ar' and X' to R, R$_1$ to R$_5$, Ar and X to obtain a compound of formula (I), (b) where R', R'$_1$ to R'$_5$, Ar' and X' are R, R$_1$, to R$_5$, Ar and X, converting any one of R, R$_1$ to R$_5$, Ar and X to another R, R$_1$ to R$_5$, Ar and X, to obtain a compound of formula (I), (c) forming a salt and/or solvate of the obtained compound of formula (Ic).

Suitable active derivatives of the compounds of formula (II) are acid halides (preferably chlorides), acid azides or acid anhydrides. Another suitable derivative is a mixed anhydride formed between the acid and an alkyl chloroformate; another suitable derivative is an activated ester such as a cyanomethyl ester, thiophenyl ester, p-nitrophenyl ester, p-nitrothiophenyl ester, 2,4,6-trichlorophenyl ester, pentachlorophenyl ester, pentafluorophenyl ester, N-hydroxyphtalimido ester, N-hydroxypiperidine ester, N-hydroxysuccinimide ester, N-hydroxy benzotriazole ester; or the carboxy group may be activated using a carbodiimide or N,N'-carbonyldiimidazole.

For example, in standard methods well known to those skilled in the art, the compounds of formula (III) may be coupled:

(a) with an acid chloride in the presence of an inorganic or organic base in a suitable aprotic solvent such as dimethylformamide (DMF) at a temperature in a range from −70 to 50° C. (preferably in a range from −10 to 20° C.), (b) with the acid in the presence of a suitable condensing agent, such as for example N,N'-carbonyl diimidazole (CDT) or a carbodiimide such as dicyclohexylcarbodiimide (DCC) or N-dimethylaminopropyl-N'-ethylcarbodiimide and N-hydroxybenzotriazole (HOBT) to maximise yields and avoid racemization processes (*Synthesis*, 453, 1972) in an aprotic solvent such as a mixture of acetonitrile (MeCN) and tetrahydrofuran (THF) in a ratio from 1:9 to 7:3, respectively, at a temperature in a range from −70 to 50° C. (preferably in a range from −10 to 25° C.) (see Scheme 1), Scheme 1

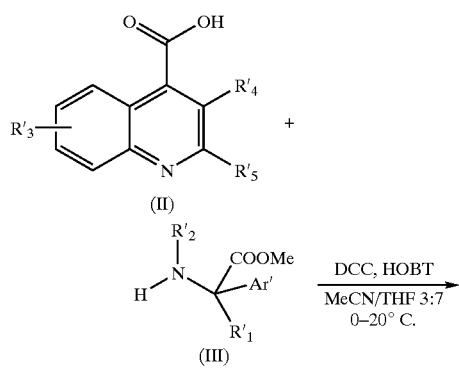

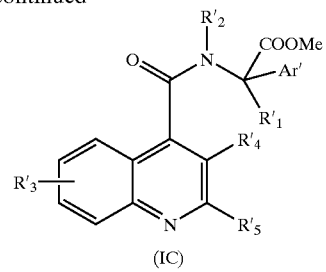

(IC)

(c) with a mixed anhydride generated in situ from the acid and an alkyl (for example isopropyl) chloroformate in a suitable aprotic solvent such as dichloromethane at a temperature in a range from −70 to 50° C. (preferably in a range from −20 to 20° C.).

It will be appreciated that a compound of formula (Ic) may be converted to a compound of formula (I), or one compound of formula (I) may be converted to another compound of formula (I), by interconversion of suitable substituents. Thus, certain compounds of formula (I) and (Ic) are useful intermediates in forming other compounds of the present invention.

For example R'$_2$ may be hydrogen and converted to R$_2$ alkyl group, for example methyl, by conventional amide alkylation procedures (Zabicky, *The chemistry of amides*; Interscience, London, 1970, p. 749). When X' is oxygen, it may be converted to X sulphur by standard thioamide formation reagents, such as P$_2$S$_5$ (*Chem. Rev.*, 61, 45, 1961 or *Angew. Chem.*, 78, 517, 1966) or the Lawesson reagent (*Tetrahedron*, 41, 5061, 1985). When Ar' or R'$_5$ is a methoxy substituted phenyl, it may be converted to another Ar' or R'$_5$ hydroxy substituted phenyl by standard demethylation procedures via Lewis acids, such as boron tribromide (*Synthesis*, 249, 1983) or mineral acids, such as hydrobromic or hydroiodic acid. When R is an alkoxycarbonyl group, for example methoxycarbonyl, it may be converted to another R, such as ethoxycarbonyl by transesterification with an appropriate alcohol at a temperature in a range from 20 to 120° C., carboxy by hydrolysis in acidic or basic medium, aminocarbonyl, alkylaminocarbonyl or dialkylaminocarbonyl by transamidation with ammonia, a primary amine or a secondary amine in methanol as solvent at a temperature in a range from 10 to 120° C., optionally in the presence of a catalytic amount of NaCN (*J. Org. Chem.* 52, 2033, 1987) or by using trimethylaluminium (Me$_3$Al) (*Tetrahedon Letters*, 48, 4171, 1977), hydroxymethyl by a selective metal hydride reduction, such as lithium borohydride reduction (*Tetrahedron*, 35. 567, 1979) or sodium borohydride reduction in THF+MeOH (*Bull. Chem. Soc. Japan*, 57, 1948, 1984 or *Synth. Commun.*, 12, 463, 1982), alkylcarbonyl by acyl chloride formation and subsequent reaction with alkylmagnesium halides in THF as solvent at a temperature in a range from −78 to 30° C. (*Tetrahedron Letters*, 4303, 1979) or with alkylcadmium halides or dialkylcadmium in the presence of MgCl$_2$ or LiCl (*J. Org. Chem*, 47, 2590, 1982). Another group which R' as methoxycarbonyl can be converted into is a substituted heteroaromatic ring, such as an oxadiazole (*J. Med. Chem.*, 34, 2726, 1991).

Scheme 2 summarizes some of the above described procedures to convert a compound of formula (Ic) or (I) in which X' is oxygen, R' is COOMe, Ar' and R'$_1$ to R'$_5$ are as described for formula (I) to another compound of formula (I).

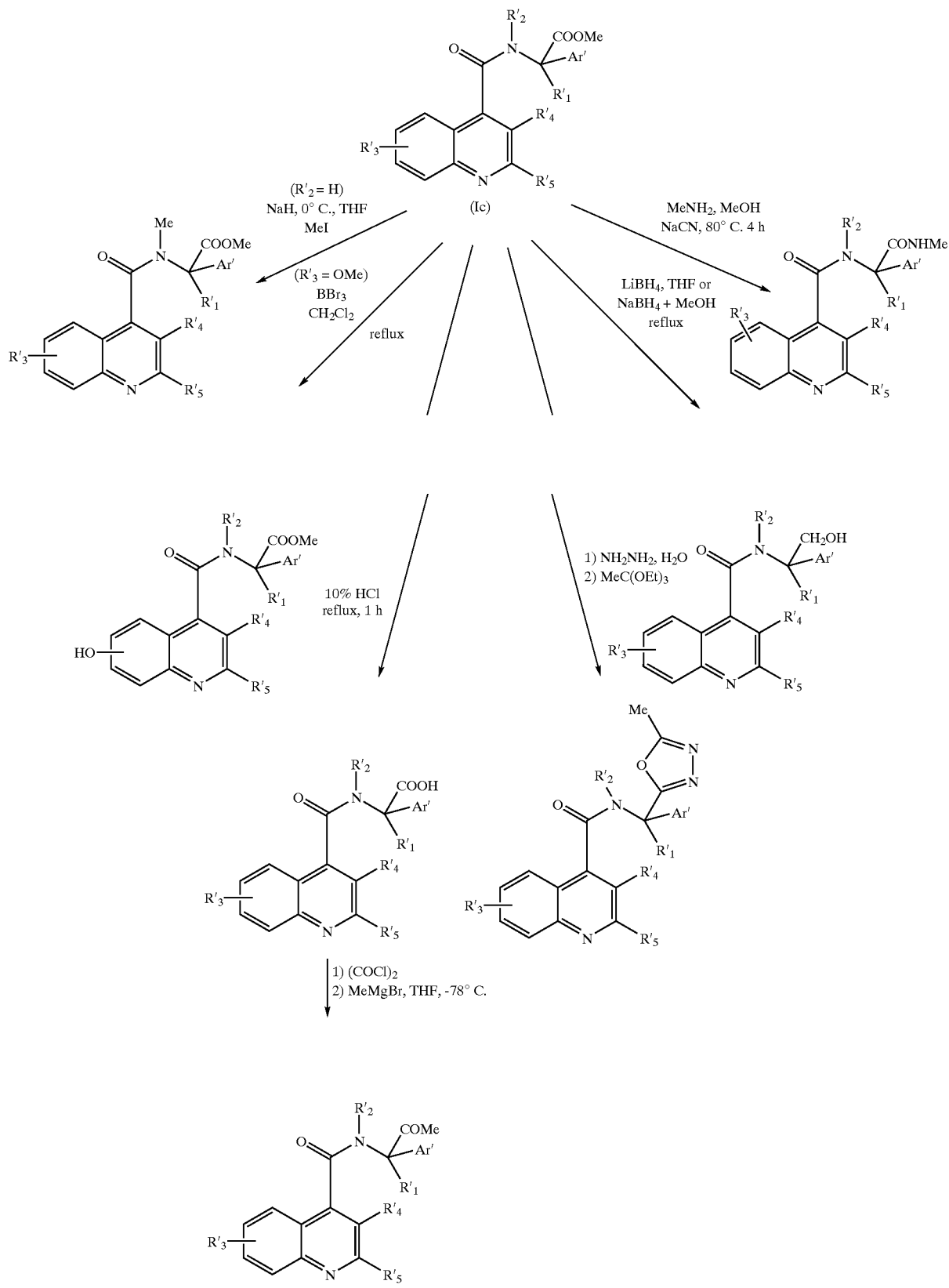

Solvates of the compounds of formula (I) may be formed by crystallization or recrystallization from the appropriate solvent. For example, hydrates may be formed by crystallization or recrystallization from aqueous solutions, or solutions in organic solvents containing water.

As mentioned before, the compounds of formula (I) may exist in more than one stereoisomeric form and the processes described herein may produce racemates as well as enantiomerically pure forms. To obtain pure enantiomers, appropriate enantiomerically pure primary or secondary amines of formula (IIId) or (IIIe)

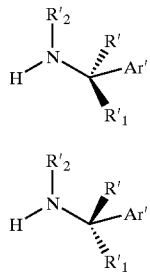

(IIId)

(IIIe)

are reacted with compounds of formula (II), to obtain compounds of formula (I'd) or (I'e).

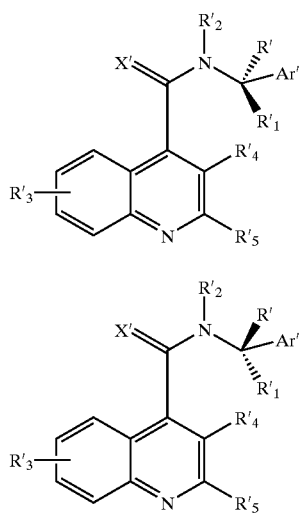

(I'd)

(I'e)

Compounds of formula (I'd) or (I'e) may subsequently be converted to compounds of formula (Id) or (Ie) by the methods of conversion mentioned before.

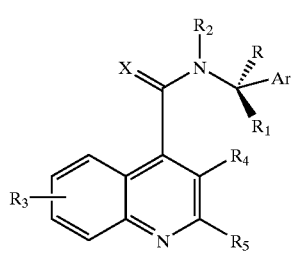

(Id)

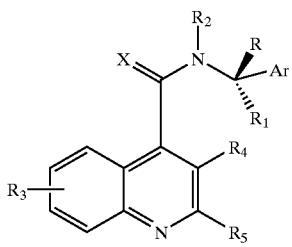

(Ie)

Compounds of formula (II) are known compounds or can be prepared from known compounds by known methods.

For example, the compound of formula (II), in which X' is oxygen, $R'_3$, $R'_4$ and $R'_5$ are hydrogen is described in Pfitzinger, *J. Prakt. Chem.*, 38, 582, 1882 and in Pfitzinger, *J. Prakt. Chem.*, 56, 293, 1897; the compound of formula (II), in which X' is oxygen, $R'_3$ and $R'_4$ are hydrogen and $R'_5$ is 2-pyridyl is described in Risaliti, *Ric. Scient.*, 28, 561, 1958; the compound of formula (II), in which X' is oxygen, $R'_3$ and $R'_4$ are hydrogen and $R'_5$ is o-, m- and p-chlorophenyl, o-fluorophenyl and 3,4-dichlorophenyl are described in Brown et al., *J. Am. Chem. Soc.*, 68, 2705, 1946; the compound of formula (II), in which X' is oxygen, $R'_3$ and $R'_4$ are hydrogen and $R'_5$ is p-methoxyphenyl is described in Ciusa and Luzzatto, *Gazz. Chim. Ital.*, 44, 64, 1914; the compound of formula (II), in which X' is oxygen, $R'_3$ and $R'_4$ are hydrogen and $R'_5$ is m-trifluoromethylphenyl is described in Shargier and Lalezari. *J. Chem. Eng. Data*, 8, 276, 1963; the compound of formula (II), in which X' is oxygen, $R'_3$ and $R'_4$ are hydrogen and $R'_5$ is p-fluorophenyl is described in Bu Hoi et al. *Rec Trav. Chim.*, 68, 781, 1949; the compound of formula (I), in which X' is oxygen, $R'_3$ and $R'_4$ are hydrogen and $R'_5$ is p-methylphenyl is described in Prevost et al., *Compt. Rend. Acad. Sci.*, 258, 954, 1964; the compound of formula (II), in which X' is oxygen, $R'_3$ and $R'_4$ are hydrogen and R'5 is p-bromophenyl is described in Nicolai et al., *Eur. J. Med. Chem.*, 27, 977, 1992; the compound of formula (II) in which X' is oxygen, $R'_4$ and $R'_5$ are hydrogen and $R'_3$ is 6-methyl is described in Buchmann and Howton, *J. Am. Chem. Soc.*, 68, 2718, 1946; the compound of formula (II). in which X' isoxygen, $R'_4$ and $R'_5$ are hydrogen and $R'_3$ is 8-nitro is described in Buchmann et al, *J. Am. Chem. Soc.*, 69, 380, 1947; the compound of formula (II), in which X' is oxygen, $R'_4$ is hydrogen, $R'_3$ is 6-chloro, $R'_5$ is p-chlorophenyl is described in Lutz et al.,*J. Am. Chem. Soc.*, 68, 1813, 1946; the compound of formula (II), in which X' is oxygen, $R'_3$ and $R'_4$ are hydrogen and $R'_5$ is 2-thiazolyl is described in Eur. Pat. Appl. EP 112,776; compounds of formula (II), in which X' is oxygen, $R'_3$ is 8-trifluoromethyl, $R'_4$ is hydrogen and $R'_5$ are phenyl, o- and p-fluorophenyl, 3,4-dichlorophenyl, p-methoxyphenyl are described in Nicolai et al., *Eur. J. Med. Chem.*, 27, 977, 1992: compounds of formula (II), in which X' is oxygen, $R'_3$ is 6-bromo, $R'_4$ is hydrogen and $R'_5$ are phenyl or p-fluorophenyl are described in Nicolai et al., *Eur. J. Med. Chem.*, 27, 977, 1992; other compounds of formula (II) are described in Ger. Offen. DE 3,721,222 and in Eur. Pat. Appl. EP 384,313.

Compounds of formula (III), (IIId) and (IIIe) are commercially available compounds or can be prepared from known compounds by known methods (for example, compounds of formula (III) in which R' is alkoxycarbonyl, $R'_1$ and $R'_2$ are hydrogen and Ar' is as defined for the compounds of formula (I), are described in *Liebigs Ann. der Chemie*, 523, 199, 1936).

The activity of the compounds of formula (A) as $NK_3$ receptor antagonists in standard tests indicates that they are of potential therapeutic utility in the treatment of Disorders herein before referred to.

Accordingly, the present invention also provides a Salt of the invention, or a pharmaceutically acceptablesolvate thereof, for use as an active therapeutic substance.

The present invention further provides a pharmaceutical composition comprising a Salt of the invention, or a pharmaceutically acceptable solvate thereof, and a pharmaceutically acceptable carrier.

The present invention also provides the use of a Salt of the invention, or a pharmaceutically acceptable solvate thereof, in the manufacture of a medicament for the treatment of the Primary, Secondary or Further Disorders disclosed herein before.

Such a medicament and a composition of this invention, may be prepared by admixture of a compound of the invention with an appropriate carrier. It may contain a diluent, binder, filler, disintegrant, flavouring agent, colouring agent, lubricant or preservative in conventional manner.

These conventional excipients may be employed for example as in the preparation of compositions of known agents for treating the conditions.

Preferably, a pharmaceutical composition of the invention is in unit dosage form and in a form adapted for use in the medical or veterinarial fields. For example, such preparations may be in a pack form accompanied by written or printed instructions for use as an agent in the treatment of the conditions.

The suitable dosage range for the compounds of the invention depends on the compound to be employed and on the condition of the patient. It will also depend, inter alia, upon the relation of potency to absorbability and the frequency and route of administration.

The compound or composition of the invention may be formulated for administration by any route, and is preferably in unit dosage form or in a form that a human patient may administer to himself in a single dosage. Advantageously, the composition is suitable for oral, rectal, topical, parenteral, intravenous or intramuscular administration. Preparations may be designed to give slow release of the active ingredient Compositions may, for example, be in the form of tablets, capsules, sachets, vials, powders, granules, lozenges, reconstitutable powders, or liquid preparations, for example solutions or suspensions, or suppositories.

The compositions, for example those suitable for oral administration, may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disinteerants, for example starch, polyvinylpyrrolidone, sodium starch glycollate or microcrystalline cellulose; or pharmaceutically acceptable setting agents such as sodium lauryl sulphate.

Solid compositions may be obtained by conventional methods of blending, filling, tabletting or the like. Repeated blending operations may be used to distribute the active agent throughout those compositions employing large quantities of fillers. When the composition is in the form of a tablet, powder, or lozenge, any carrier suitable for formulating solid pharmaceutical compositions may be used, examples being magnesium stearate, starch, glucose, lactose, sucrose, rice flour and chalk. Tablets may be coated according to methods well known in normal pharmaceutical practice, in particular with an enteric coating. The composition may also be in the form of an ingestible capsule, for example of gelatin containing the compound, if desired with a carrier or other excipients.

Compositions for oral administration as liquids may be in the form of, for example, emulsions, syrups, or elixirs, or may be presented as a dry product for reconstitution with water or other suitable vehicle before use. Such liquid compositions may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; aqueous or non-aqueous vehicles, which include edible oils, for example almond oil, fractionated coconut oil, oily esters, for example esters of glycerine, or propylene glycol, or ethyl alcohol, Glycerine, water or normal saline; preservatives, for example methyl or propyl p-hydroxybenzoate or sorbic acid; and if desired conventional flavouring or colouring agents.

The compounds of this invention may also be administered by a non-oral route. In accordance with routine pharmaceutical procedure, the compositions may be formulated, for example for rectal administration as a suppository. They may also be formulated for presentation in an injectable form in an aqueous or non-aqueous solution, suspension or emulsion in a pharmaceutically acceptable liquid, e.g. sterile pyrogen-free water or a parenterally acceptable oil or a mixture of liquids. The liquid may contain bacteriostatic agents, anti-oxidants or other preservatives, buffers or solutes to render the solution isotonic with the blood, thickening agents, suspending agents or other pharmaceutically acceptable additives. Such forms will be presented in unit dose form such as ampoules or disposable injection devices or in multi-dose forms such as a bottle from which the appropriate dose may be withdrawn or a solid form or concentrate which can be used to prepare an injectable formulation.

The compounds of this invention may also be administered by inhalation, via the nasal or oral routes. Such administration can be carried out with a spray formulation comprising a compound of the invention and a suitable carrier, optionally suspended in, for example, a hydrocarbon propellant.

Preferred spray formulations comprise micronised compound particles in combination with a surfactant, solvent or a dispersing agent to prevent the sedimentation of suspended particles. Preferably, the compound particle size is from about 2 to 10 microns.

A further mode of administration of the compounds of the invention comprises transdermal delivery utilising, a skin-patch formulation. A preferred formulation comprises a compound of the invention dispersed in a pressure sensitive adhesive which adheres to the skin, thereby permitting the compound to diffuse from the adhesive through the skin for delivery to the patient. For a constant rate of percutaneous absorption, pressure sensitive adhesives known in the art such as natural rubber or silicone can be used.

As mentioned above, the effective dose of compound depends on the particular compound employed, the condition of the patient and on the frequency and route of administration. A unit dose will generally contain from 20 to 1000 mg and preferably will contain from 30 to 500 mg, in particular 50, 100, 150, 200, 250, 300, 350, 400, 450, or 500 mg. The composition may be administered once or more times a day for example 2, 3 or 4 times daily, and the total daily dose for a 70 ka adult will normally be in the range 100 to 3000 mg. Alternatively the unit dose will contain from 2 to 20 mg of active ingredient and be administered in multiples, if desired, to give the preceding daily dose.

No unacceptable toxicological effects are expected with compounds of the invention when administered in accordance with the invention.

The present invention also provides a method for the treatment and/or prophylaxis of the Primary, Secondary or Further Disorders in mammals, particularly humans, which comprises administering to the mammal in need of such treatment and/or prophylaxis an effective, non-toxic pharmaceutically acceptable amount of a Salt of the invention or a pharmaceutically acceptable solvate thereof.

The activity of the compounds of the present invention, as $NK_3$ ligands, is determined by their ability to inhibit the binding of the radiolabelled $NK_3$ ligands, [$^{125}I$]-[Me-Phe$^7$]-NKB or [$^3H$]-Senktide, to guinea-pig and human $NK_3$ receptors (Renzetti et al, 1991, *Neuropeptide* 18, 104–114; Buell et al, 1992, *FEBS*, 299(1), 90–95; Chung et al, 1994. *Biochem. Biophys. Res. Commun.*, 198(3), 967–972). The binding assays utilized allow the determination of the concentration of the individual compound required to reduce by 50% the [$^{125}I$]-[Me-Phe$^7$]-NKB and [$^3H$]-Senktide specific binding to $NK_3$ receptor in equilibrium conditions (IC50). Binding assays provide for each compound tested a mean $IC_{50}$ value of 2–5 separate experiments performed in duplicate or triplicate. The most potent compounds of the present invention show $IC_{50}$ value, in the range 1–1000 nM; in particular, in guinea-pig cortex membranes by displacement of [$^3H$]-Senktide, the compound of the Example 1 displays a $K_i$ of 4.8 nM (n=3). The $NK_3$-antagonist activity of the compounds of the present invention is determine by their ability to inhibit senktide-induced contraction of the guinea-pig ileum (Maggi et al. 1990, *Br. J. Pharmacol.*, 101, 996–1000) and rabbit isolated iris sphincter muscle (Hall et al., 1991, *Eur. J. Pharmacol.*, 199, 9–14) and human $NK_3$ receptors-mediated $Ca^{++}$ mobilization (Mochizuki et al. 1994, *J. Biol. Chem.*, 269, 9651–9658). Guinea-pig and rabbit in-vitro functional assays provide for each compound tested a mean $K_B$ value of 3–8 separate experiments, where $K_B$ is the concentration of the individual compound required to produce a 2-fold rightward shift in the concentration-response curve of senktide. Human receptor functional assay allows the determination of the concentration of the individual compound required to reduce by 50% ($IC_{50}$ values) the $Ca^{++}$ mobilization induced by the agonist NKB. In this assay, the compounds of the present invention behave as antagonists.

The therapeutic potential of the compounds of the present invention in treating the conditions can be assessed using rodent disease models.

The following Description illustrates the preparation of an intermediate, whereas the Example illustrates the preparation of a compound of the present invention but they do not limit the invention in any way.

Experimental Details

DESCRIPTION 1

(S)-(−)-N-(α-Ethylbenzyl)-3-hydroxy-2-phenyl-4-quinoline Carboxamide 2.49 g (9.4 mmols) of 3-hydroxy-2-phenyl-4-quinoline carboxylic acid (CAS [485-89-2]) were suspended in 150 ml of a mixture of THF/MeCN 7:3, respectively; 1.40 g (10.3 mmols) of 1-hydroxybenzotriazole (HOBT) were added to the suspension and then 1.27 g (9.4 mmols) of (S)-(−)-1-phenylpropylamine, dissolved in 20 ml of methylene chloride were added dropwise over 10 minutes period. The reaction mixture was stirred at room temperature for 30 minutes and then 2.13 g (10.3 mmols) of dicyclohexylcarbodiimide (DCC), dissolved in 20 ml of methylene chloride, were added dropwise and the reaction stirred overnight. 20 ml of $H_2O$ were added and the reaction stirred 30 minutes, then the solvent was evaporated in vacuo to dryness. The residue was taken up in EtOAc, the precipitated dicyclohexylurea (DCU) was filtered off and the filtrate washed with water, 20% citric acid, 5% $NaHCO_3$, brine and the organic layer dried over $Na_2SO_4$ and the solvent evaporated in vacuo. The residue was purified by silica-gel (60–240 mesh) flash column chromatography, eluting with a mixture of hexane/EtOAc 9:1, containing increasing amounts of EtOAc, until the ratio 7:3. The purified product was crystallized from i-PrOH to yield 1.75 g of the title compound as a white solid.

$C_{25}H_{22}N_2O_2$;

M.P.=168–168.4° C.;

M.W.=382.47;

 =−28.5 (c=0.5, MeOH);

Elemental analysis: Calcd. C, 78.51; H, 5.80; N, 7.33; Found C, 78.49; H, 5.84; N, 7.86.

I.R. (Kbr): 3370; 1625; 1525 cm$^{-1}$.

300 MHz $^1$H-NMR (DMSO-d$_6$): δ: 9.80 (s, 1H); 9.11 (d, 1H); 8.00–7.94 (m, 3H); 7.61–7.42 (m, 8H); 7.38 (dd, 2H); 7.28 (dd, 1H); 5.06 (dt, 1H), 1.82 (ddq, 2H); 0.97 (t, 3H).

MS (EI; TSQ 700: source 200° C.; 70 eV; 200 μA): 382 (M+.); 264; 247; 219.

EXAMPLE 1

(S)-(+)-N-(α-Ethylbenzyl)-3-hydroxy-2-phenyl-4-quinoline Carboxamide Sodium Salt Sesquihydrate 500 mg (1.31 mmols) of (S)-(−)-N-(α-ethylbenzyl)-3-hydroxy-2-phenyl-4-quinoline carboxamide (the compound of Description 1), dissolved in 20 ml of MeOH containing 1.31 ml of 1N NaOH (1.31 mmols). were stirred at 40° C. for 30 minutes and then the solvent was evaporated in vacuo to dryness. Crystallization of the residue from a mixture of toluene and iPrOH yielded 240 mg of the title compound as a yellow solid.

$C_{25}H_{22}N_2O_2Na.1.5\ H_2O$;

M.P.=110° C. (dec.);

M.W.=431.48;

 =+169.81 (c=0.5, MeOH);

Elemental analysis: Calcd. C, 69.59; H, 5.61; N, 6.49; Na, 5.33;

Found C, 69.07; H, 5.45; N, 6.05; Na, 5.49.

I.R. (nujol): 1640; 1460; 1380 cm−1.

300 MHz $^1$H-NMR (DMSO-d$_6$): δ: 13.3 (d, 1H); 9.4 (d, 1H); 8.23 (d, 2H); 7.60 (dd, 1H); 7.41–7.09 (m, 9H); 6.09 (ddd, 1H); 5.08 (dt, 1H); 1.80 (m, 2H); 0.91 (t, 3H).

What is claimed is:

1. A method for the treatment or prophylaxis of disorders in mammals, said disorders selected from pulmonary disorders, skin disorders and itch, neurogenic inflammation and CNS disorders, which method comprises administering to the mammal in need of such treatment or prophylaxis an effective, non-toxic pharmaceutically acceptable amount of a salted form of (S)-(+)-N-(α-ethylbenzyl)-3-hydroxy-2-phenyl-4-quinoline or a solvate thereof, characterized in that the salt comprises (S)-(+)-N-(α-ethylbenzyl)-3-hydroxy-2-phenyl-4-quinoline in anionic form and a pharmaceutically acceptable salting cation.

2. A method for the treatment or prophylaxis of disorders in mammals, said disorders selected from convulsive disorders, renal disorders, urinary incontinence, ocular inflammation, inflammatory pain, eating disorders, allergic rhinitis, neurodegenerative disorders, psoriasis, Huntington's disease, and depression, which method comprises administering to the mammal in need of such treatment or prophylaxis an effective, non-toxic pharmaceutically acceptable amount of a salted form of (S)-(+)-N-(α-ethylbenzyl)-3-hydroxy-2-phenyl-4-quinoline or a solvate thereof, characterized in that the salt comprises (S)-(+)-N-(α-ethylbenzyl)-3-hydroxy-2-phenyl-4-quinoline in anionic form and a pharmaceutically acceptable salting cation.

3. A method for the treatment or prophylaxis of disorders in mammals, said disorders selected from schizophrenia, AIDS related dementia, senile dementia of the Alzheimer type, Down's syndrome, demyelinating diseases, diabetic or peripheral neuropathy, AIDS related neuropathy, chemotherapy-induced neuropathy and neuralgia, bronchopneumonia and bronchospasm, inflammatory bowel disease, fibrositis, osteoarthritis, rheumatoid arthritis, eczema, poison ivy, conjunctivitis, vernal conjuctivitis, contact dermatitis, urticaria and other eczematoid dermatitis, alcoholism, stress related somatic disorders, reflex sympathetic dystrophy, dysthymic disorders, rejection of transplanted tissues and disorders related to immune enhancement or suppression, gastrointestinal (GI) disorders and diseases of the GI tract, disorders of the bladder function, fibrosing and collagen diseases, disorders of the blood flow caused by vasodilation and vasospastic diseases, migraine and Reynaud's disease, pain or nociception, which method comprises administering to the mammal in need of such treatment or prophylaxis an effective, non-toxic pharmaceutically acceptable amount of a salted form of (S)-(+)-N-(α-ethylbenzyl)-3-hydroxy-2-phenyl-4-quinoline or a solvate thereof, characterized in that the salt comprises (S)-(+)-N-(α-ethylbenzyl)-3-hydroxy-2-phenyl-4-quinoline in anionic form and a pharmaceutically acceptable salting cation.

* * * * *